United States Patent
Mathur et al.

(10) Patent No.: US 9,738,662 B2
(45) Date of Patent: Aug. 22, 2017

(54) PROCESS FOR PRODUCING TETRAKIS($^F$ARYL)BORATE SALTS

(71) Applicant: Albemarle Corporation, Baton Rouge, LA (US)

(72) Inventors: Rajeev S. Mathur, Baton Rouge, LA (US); Jamie R. Strickler, Baton Rouge, LA (US)

(73) Assignee: ALBEMARLE CORPORATION, Baton Rouge, LA (US)

( * ) Notice: Subject to any disclaimer, the term of this patent is extended or adjusted under 35 U.S.C. 154(b) by 93 days.

(21) Appl. No.: 14/434,132

(22) PCT Filed: Nov. 8, 2013

(86) PCT No.: PCT/US2013/069177
§ 371 (c)(1),
(2) Date: Apr. 8, 2015

(87) PCT Pub. No.: WO2014/085058
PCT Pub. Date: Jun. 5, 2014

(65) Prior Publication Data
US 2015/0259362 A1    Sep. 17, 2015

Related U.S. Application Data

(60) Provisional application No. 61/730,203, filed on Nov. 27, 2012, provisional application No. 61/774,877, filed on Mar. 8, 2013.

(51) Int. Cl.
*C07F 5/02* (2006.01)

(52) U.S. Cl.
CPC .............. *C07F 5/02* (2013.01); *C07F 5/027* (2013.01)

(58) Field of Classification Search
None
See application file for complete search history.

(56) References Cited

U.S. PATENT DOCUMENTS

| | | | |
|---|---|---|---|
| 5,488,169 A | 1/1996 | Ikeda et al. | |
| 5,693,261 A | 12/1997 | Krzystowczyk et al. | |
| 6,129,863 A | 10/2000 | Lee et al. | |
| 6,162,950 A | 12/2000 | Lee et al. | |
| 6,169,208 B1 | 1/2001 | Lee | |
| 6,231,790 B1 | 5/2001 | Askham | |
| 6,235,222 B1 | 5/2001 | Mitsui et al. | |
| 6,241,917 B1 | 6/2001 | Owens et al. | |
| 6,248,265 B1 * | 6/2001 | Lee | C07F 3/02 260/1 |
| 6,831,200 B2 | 12/2004 | Lee et al. | |
| 7,087,780 B2 | 8/2006 | Lee et al. | |
| 7,205,441 B2 * | 4/2007 | Ikeno | C07F 5/027 568/1 |
| 2003/0216598 A1 * | 11/2003 | Ikeno | C07F 5/027 568/1 |
| 2004/0068134 A1 | 4/2004 | Lee et al. | |
| 2007/0197831 A1 | 8/2007 | Lee et al. | |
| 2008/0177015 A1 | 7/2008 | Lewis | |

FOREIGN PATENT DOCUMENTS

| | | |
|---|---|---|
| CA | 2243659 A1 | 11/1997 |
| GB | 986949 | 3/1965 |
| GB | 1012376 | 12/1965 |
| WO | 2007/070770 A1 | 6/2007 |

OTHER PUBLICATIONS

Corey-House Synthesis, http://en.wikipedia.org/wiki/Corey-House_synthesis, website visited Oct. 12, 2012, 2 pages.
Cairncross, A., et al., "Pentafluorophenylcopper Tetramer, A Reagent for Synthesis of Fluorinated Aromatic Compounds", Organic Synthesis, Coll. vol. 6, p. 875, (1988); vol. 59, p. 122 (1979).
DePasquale, R.J., et al., "Reactions of Pentafluorophenylcopper Reagent", The Journal of Organic Chemistry, vol. 34, No. 6, Jun. 1969, pp. 1736-1740.
Harper, Jr., R. J., et al., "Reactions of Organometallics with Fluoroaromatic Compounds", J. of Organic Chemistry, vol 29, No. 8, 1964, pp. 2385-2389.
Respess, W.L., et al., "A New Synthesis of Perfluoroaromatic Grignard Reagents", J. of Organic Chemistry, vol. 18, 1969, pp. 263-274.
Respess, W.L., et al., "Synthesis of Pentafluorophenylmagnesium Compounds", J. Organometal. Chem. 11, 1968, pp. 619-622.
Sandararaman, A., et al., "A Comparative Study of Base-Free Arylcopper Reagents for the Transfer of Aryl Groups to Boron Halides", J. of Organometallic Chemistry, 681, 2003, pp. 134-142.
Tamura, M., et al., "Copper-Catalyzed Coupling of Grignard Reagents and Alkyl Halides in Tetrahydrofuran Solutions", J. of Organometallic Chemistry, 42, 1972, pp. 205-228.
Wakami, H., et al., "Grignard Exchange Reaction Using a Microflow System: From Bench to Pilot Plant", Organic Process Research & Development, 9, 2005, pp. 787-791.

* cited by examiner

*Primary Examiner* — Joseph D Anthony
(74) *Attorney, Agent, or Firm* — Jeremy J. Kliebert

(57) ABSTRACT

This invention provides processes for forming halomagnesium tetrakis($^F$aryl)borates, which processes comprise bringing together, in an anhydrous liquid organic medium, at least one boron trihalide; at least one $^F$aryl Grignard reagent; and at least one copper compound. Also provided are processes for forming halomagnesium tetrakis($^F$aryl)borates, which processes comprise bringing together, in an anhydrous liquid organic medium, at least one boron trihalide; at least one copper compound; magnesium metal; and at least one polyhaloaromatic compound.

11 Claims, No Drawings

PROCESS FOR PRODUCING TETRAKIS($^F$ARYL)BORATE SALTS

REFERENCE TO RELATED APPLICATIONS

This application is the National Stage of International Patent Appl. No. PCT/US2013/069177 filed on Nov. 8, 2013, which in turn claims the benefit of U.S. Provisional Patent Appl. No. 61/730,203, filed on Nov. 27, 2012, and U.S. Provisional Patent Appl. No. 61/774,877, filed Mar. 8, 2013, the disclosures of which are incorporated herein by reference.

TECHNICAL FIELD

This invention relates to methods for preparing tetrakis($^F$aryl)borate salts via $^F$aryl Grignard reagents.

BACKGROUND

Some metal and metalloid polyfluoroaryl compounds are used as activators for polymerization catalysts. Polyfluoroaryl Grignard reagents are useful in the synthesis of tetrakis(polyfluoroaryl)borate salts, from which metal and metalloid polyfluoroaryl compounds are made. When forming tetrakis(polyfluoroaryl)borate salts from a boron trihalide and a polyfluoroaryl Grignard reagent, elevated temperatures are usually needed to drive the reaction to completion (in the sense of adding four groups to boron). However, operating at elevated temperatures causes degradation of the polyfluoroaryl Grignard reagent, which increases the amount of polyfluoroaryl Grignard reagent consumed, thereby increasing production costs.

SUMMARY OF THE INVENTION

This invention provides facile, high-yield processes for forming halomagnesium tetrakis($^F$aryl)borate salts from a boron trihalide and a $^F$aryl Grignard reagent in the presence of copper catalysts. The processes of this invention proceed relatively quickly at ambient temperature, providing economic advantages. Cost improvements are a result of better Grignard utilization, lower temperatures, reduced cycle times, and at least in some instances, high pressure equipment is not needed. Another advantage is that residual copper does not seem to interfere in downstream processes that utilize the halomagnesium tetrakis($^F$aryl)borates produced by this invention.

An embodiment of this invention is a process for forming halomagnesium tetrakis($^F$aryl)borates. The process comprises bringing together, in an anhydrous liquid organic medium, at least one boron trihalide; at least one $^F$aryl Grignard reagent; and at least one copper compound.

These and other embodiments and features of this invention will be still further apparent from the ensuing description and appended claims.

FURTHER DETAILED DESCRIPTION OF THE INVENTION

Throughout this document, the term "$^F$aryl group" shall be understood, when not specified, to mean, as described above, a fluorine-containing aryl group, which has at least two fluorine atoms, or at least two perfluorohydrocarbyl groups, or at least one fluorine atom and at least one perfluorohydrocarbyl group, bonded directly to an aromatic ring. It is preferred that at least two fluorine atoms or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The aromatic ring of the $^F$aryl group may be, but is not limited to, benzene, naphthalene, anthracene, biphenyl, phenanthrene, or indene. Benzene is a preferred aromatic moiety; naphthalene is another preferred moiety. The perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. The hydrocarbyl groups of the aryl groups are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The silyl groups preferably have $C_1$ to $C_{18}$ alkyl groups or $C_6$ to $C_{20}$ aryl or aralkyl groups. Suitable silyl groups include trimethylsilyl, triisopropylsilyl, tert-butyl(dimethyl)silyl, tridecylsilyl, and triphenylsilyl. Examples of $^F$aryl groups that may be present on the borate moiety in this invention include 3,5-bis(trifluoromethyl)phenyl, 2,4,6-tris(trifluoromethyl)-phenyl, 4-[tri(isopropyl)silyl]-tetrafluorophenyl, 4-[dimethyl(tert-butyl)silyl]-tetrafluorophenyl, 4'-(methoxy)-octafluoro-1-biphenyl-4-yl, 2,3-bis(pentafluoroethyl)-naphthyl, 2-(isopropoxy)-hexafluoronaphthyl, 9,10-bis(heptafluoropropyl)-heptafluoroanthryl, 9,10-bis(p-tolyl)-heptafluorophenanthryl, and 1-(trifluoromethyl)-tetrafluoroindenyl.

It is preferred that at most two substituents on the ring of the $^F$aryl group are hydrocarbyl, perfluorohydrocarbyl, or alkoxy, while the rest of the substituents are fluorine atoms. Preferred $^F$aryl groups are those in which the all of the substituents are fluorine atoms. Examples of such groups are pentafluorophenyl, nonafluoro-1-biphenyl-4-yl, nonafluoro-1-biphenyl-3-yl, 1-heptafluoronaphthyl, 2-heptafluoronaphthyl, 7-nonafluoroanthryl, 9-nonafluorophenanthryl, and analogous groups. Preferred perfluoroaryl groups include pentafluorophenyl and heptafluoronaphthyl groups.

The liquid organic medium is preferably an ether-containing medium. This medium may be comprised of one or more ethers, and may, at various points, also contain one or more other types of components, such as hydrocarbons or hydrocarbyl halides. Any of a variety of monoethers or polyethers may be used, including diethyl ether, diisopropyl ether, dibutyl ether, tetrahydrofuran, 1,4-dioxane, cyclohexylmethyl ether, diglyme, triglyme, and tetraglyme. Diethyl ether is a preferred liquid organic medium in the practice of this invention.

In the practice of this invention, boron trihalides include boron trifluoride, boron trichloride, boron tribromide, boron triiodide, or any mixed-halogen boron trihalide, as well as the solvent-complexed forms of these compounds. A preferred boron trihalide in the practice of this invention is boron trifluoride and its solvent complexes, such as boron trifluoride diethyl etherate complex.

The boron trihalide or its solvent complex may be dissolved in a solvent. Preferred solvents are ethers; a preferred ether is diethyl ether. Because the boron trihalide (whether solvent-complexed and/or whether in solution) will be mixed with an $^F$aryl Grignard reagent, the boron trihalide is normally anhydrous, although traces of moisture can be tolerated. If the boron trihalide is too wet or the reaction zone contains moisture, the amount of $^F$aryl Grignard reagent needs to be increased to maintain the desired ratio of $^F$aryl Grignard reagent to boron trihalide.

As used throughout this document, the term "$^F$aryl Grignard reagent" refers to a halomagnesium $^F$aryl compound, which nominally contains a halogen atom in anion form, a magnesium cation, and a $^F$aryl group. The $^F$aryl group and the preferences therefor are as described above. In the $^F$aryl Grignard reagent, the halogen atom of the halomagnesium moiety of the $^F$aryl Grignard reagent may be a chlorine atom, bromine atom, or iodine atom. Preferred halogen atoms are chlorine and bromine; more preferred is a bromine atom. Thus, preferred halomagnesium moieties include chloromagnesium moieties and bromomagnesium moieties.

The $^F$aryl Grignard reagents can be formed by several routes. One way is via reaction of magnesium metal and at least one polyhaloaromatic compound in which one position on the aromatic ring(s) is substituted by a halogen atom other than a fluorine atom, and in which each of the other positions on the aromatic ring(s) is substituted by a fluorine atom, a hydrocarbyl group, an alkoxy group, or a perfluorinated hydrocarbyl group, in an anhydrous liquid organic medium.

Another way of forming the $^F$aryl Grignard reagents used in the processes of this invention comprises bringing together, in a liquid organic medium, a hydrocarbyl Grignard reagent, and at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group as described above, including preferences therefor, in an anhydrous liquid organic medium, to form a $^F$aryl Grignard reagent. When forming $^F$aryl Grignard reagents by this method, the resultant mixture is composed predominately of $^F$aryl magnesium halide (the $^F$aryl Grignard reagent), hydrocarbyl halide, polyhaloaromatic compound, and liquid organic medium. See U.S. Pat. No. 6,129,863 in connection with preparation of $^F$aryl Grignard reagents by this route. A preferred hydrocarbyl Grignard reagent is isopropylmagnesium bromide, and a preferred liquid organic medium is a liquid ethereal reaction medium.

Suitable polyhaloaromatic compounds are analogous to the $^F$aryl groups described above, with a halogen atom other than a fluorine atom in one position on the aromatic ring. It is preferred that at most two substituents on the ring of the polyhaloaromatic compound are hydrocarbyl, perfluorohydrocarbyl, or alkoxy, while the rest of the substituents are fluorine atoms. Preferred polyhaloaromatic compounds are those in which the all of the substituents are fluorine atoms except for the halogen atom other than a fluorine atom in one position on the aromatic ring. Examples of such compounds are chloropentafluorobenzene, bromopentafluorobenzene, 4-chlorononafluoro-1-biphenyl, 4-bromononafluoro-1-biphenyl, 3-chlorononafluoro-1-biphenyl, 3-bromononafluoro-1-biphenyl, 1-chloroheptafluoronaphthylene, 1-bromoheptafluoronaphthylene, 2-chloroheptafluoronaphthylene, 2-bromoheptafluoronaphthylene, 7-chlorononafluoro-anthracene, 7-bromononafluoroanthracene, 9-chlorononafluorophen-anthrene, 9-bromononafluorophenanthrene, and analogous compounds. Preferred polyfluoroaryl compounds include chloropentafluorobenzene, bromopentafluorobenzene, chloroheptafluoronaphthylene, and bromoheptafluoronaphthylene.

Preferred $^F$aryl Grignard reagents include pentafluorophenyl chloromagnesium, pentafluorophenyl bromomagnesium, 1-nonafluorobiphenyl-4-yl chloromagnesium, 1-nonafluorobiphenyl-4-yl bromomagnesium, nonafluoro-1-biphenyl-3-yl chloromagnesium, nonafluoro-1-biphenyl-3-yl bromomagnesium, 1-heptafluoronaphthyl bromomagnesium, 1-heptafluoronaphthyl chloromagnesium, 2-heptafluoronaphthyl bromomagnesium, 2-heptafluoronaphthyl chloromagnesium, 7-nonafluoroanthryl chloromagnesium, 7-nonafluoroanthryl bromomagnesium, 9-nonafluorophenanthryl chloromagnesium, 9-nonafluorophenanthryl bromomagnesium, 3,5-bis(trifluoromethyl)phenyl chloromagnesium, 2,4,6-tris(trifluoromethyl)-phenyl bromomagnesium, 4-[tri(isopropyl)silyl]-tetrafluorophenyl chloromagnesium, 4-[dimethyl(tert-butyl)silyl]-tetrafluorophenyl bromomagnesium, 4'-(methoxy)-octafluoro-1-biphenyl-4-yl chloromagnesium, 2,3-bis(pentafluoroethyl)-naphthyl bromomagnesium, 2-(isopropoxy)-hexafluoronaphthyl chloromagnesium, 9,10-bis(heptafluoropropyl)-heptafluoroanthryl bromomagnesium, 9,10-bis(p-tolyl)-heptafluorophenanthryl chloromagnesium, and 1-(trifluoromethyl)-tetrafluoroindenyl bromomagnesium. More preferred Grignard reagents include 1-heptafluoronaphthyl bromomagnesium, 1-heptafluoronaphthyl chloromagnesium, 2-heptafluoronaphthyl bromomagnesium, 2-heptafluoronaphthyl chloromagnesium, pentafluorophenyl bromomagnesium and pentafluorophenyl chloromagnesium, especially 1-heptafluoronaphthyl bromomagnesium, 2-heptafluoronaphthyl bromomagnesium, and pentafluorophenyl bromomagnesium, and more especially pentafluorophenyl bromomagnesium. Mixtures of $^F$aryl Grignard reagents can be used, and will result in tetrakis($^F$aryl)borates with mixtures of $^F$aryl groups.

The $^F$aryl Grignard reagent is usually in an anhydrous solvent, preferably the liquid organic medium for the processes of this invention, as described above.

Both copper(I) and copper(II) compounds can be used as catalysts in the processes of this invention. Any of a large number of copper compounds can be used. The presence of hydrates and/or other species that consume Grignard reagents are acceptable in the practice of this invention because the amount of copper compound is quite small relative to the amount of Grignard reagent. If desired, mixtures of copper compounds can be used, including mixtures of copper(I) and copper(II) compounds.

The amount of copper relative to the Grignard reagent is a catalytic amount. A catalytic amount is typically about 0.001 mmol or more of copper, preferably about 0.005 mmol or more of copper, per mole of Grignard reagent. Often, in the range of about 0.001 mmol to about 40 mmol of copper, preferably in the range of about 0.005 mmol to about 40 mmol of copper, per mole of Grignard reagent is employed. Larger amounts of copper can be used, but do not further increase the beneficial effects provided by this invention. More preferably, about 0.01 mmol to about 20 mmol of copper, still more preferably about 0.1 mmol to about 15 mmol of copper, is employed per mole of Grignard reagent.

When a Grignard reagent is not formed prior to combination with the other ingredients in the process (the processes in which the polyhaloaromatic compound is added later), the amount of copper relative to the polyhaloaromatic compound is a catalytic amount; the amounts of copper to the polyhaloaromatic compound and preferences therefor are the same as those described for the relative amounts of copper to the Grignard reagent. As described with regard to the Grignard reagent, larger amounts of copper can be used, but do not further increase the beneficial effects provided by this invention.

Suitable copper(I) compounds in the practice of this invention include, but are not limited to, copper(I) chloride, copper(I) bromide, copper(I) iodide, copper(I) cyanide, copper(I) thiocyanate, copper(I) oxide, copper(I) sulfide, copper (I) selenide, copper(I) telluride, copper(I) acetate, copper(I) 3-methylsalicylate, copper(I) thiophenolate, bromotris(triphenylphosphine)copper(I), bis(triphenylphosphine)copper (I) nitrate, bis(triphenylphosphine)copper(I) tetrahydridoborate, copper(I) trifluoromethanesulfonate benzene or toluene complex, 1,4-diazabicyclo[2.2.2]octane)copper(I)chloride complex (also called DABCO®-copper(I) chloride complex), bromo(1,10-phenanthroline)(triphenylphosphine) copper(I), copper(I) bromide dimethyl sulfide complex, copper(I) iodide dimethyl sulfide complex, copper(I) iodide trimethylphosphite complex, iodo(triethyl phosphite)copper (I), bis(triphenylphosphine)copper(I) nitrate, tetrakis(acetonitrile)copper(I) tetrafluoroborate, tetrakis(acetonitrile) copper(I) hexafluorophosphate, tetrakis(acetonitrile)copper (I) trifluoromethanesulfonate, tetrakis(pyridine)copper(I) trifluoromethanesulfonate, bis[(tetrabutylammonium iodide)copper(I) iodide], mesitylcopper(I), cyclopentadienyl (triethylphosphine)copper(I), ethylcyclopentadienyl)(triphenylphosphine)copper(I), copper(I) thiophene-2-carboxylate, and the like.

Preferred copper(I) compounds are copper(I) halides and complexes thereof, including copper(I) chloride, copper(I) bromide, copper(I) iodide, bromotris(triphenylphosphine) copper(I), 1,4-diazabicyclo[2.2.2]octane)copper(I)chloride complex, bromo(1,10-phenanthroline)(triphenylphosphine) copper(I), copper(I) bromide dimethyl sulfide complex, copper(I) iodide dimethyl sulfide complex, copper(I) iodide trimethylphosphite complex, iodo(triethyl phosphite)copper (I), and bis[(tetrabutylammonium iodide)copper(I) iodide]. More preferred copper(I) compounds include copper(I) chloride, copper(I) bromide, and bromotris(triphenylphosphine)copper(I).

Suitable copper(II) compounds in the practice of this invention include, but are not limited to, copper(II) chloride, copper(II) bromide, copper(II) iodide, copper(II) carbonate, copper(II) nitrate, copper(II) hydroxide, copper(II) oxide, copper(II) sulfide, copper(II) selenide, copper(II) sulfate, copper(II) phosphate, copper(II) tetrafluoroborate, copper (II) trifluoromethanesulfonate, copper(II) acetate, copper(II) trifluoroacetate, copper(II) formate, copper(II) oxalate, copper(II) tartrate, copper(II) 2-ethylhexanoate, copper(II) isobutyrate, copper(II) 3,5-diisopropylsalicylate, copper(II) acrylate, copper(II) methacrylate, copper(II) acetylacetonate, copper(II) hexafluoroacetylacetonate, copper(II) tert-butylacetoacetate, copper(II) ethylacetoacetate, bis(acetylacetonato)copper(II), bis(t-butylacetoacetato)copper(II), ammonium copper(II) chloride, ammonium tetrachlorocuprate(II), bis(ethylenediamine)copper(II) hydroxide, tetraamminecopper(II) sulfate, ammonium copper(II) sulfate, and the like.

Preferred copper(II) compounds are copper(II) halides and complexes thereof, including copper(II) chloride, copper(II) bromide, copper(II) iodide, ammonium copper(II) chloride, and ammonium tetrachlorocuprate(II). More preferred copper(II) compounds include copper(II) chloride and copper(II) bromide.

In the processes of this invention, at least one boron trihalide, at least one $^F$aryl Grignard reagent, and at least one copper compound are brought together in an anhydrous liquid organic medium. In the process, the boron trihalide and the $^F$aryl Grignard reagent are in proportions such that a salt of a tetrakis($^F$aryl)borate anion is produced.

A feature of this invention is the formation of tetrakis ($^F$aryl)borate anions, usually without co-formation of detectable amounts of tris($^F$aryl)boranes. Molar ratios of $^F$aryl Grignard reagent to boron trihalide of about 3.8:1 or less yield larger amounts of the corresponding di($^F$aryl)haloborane, a side product. Preferred molar ratios of Grignard reagent to boron trihalide are in the range of about 3.9:1 to about 4.5:1, more preferably about 4.0:1 to about 4.1:1. When a Grignard reagent is not formed prior to combination with the other ingredients in the process (the processes in which the polyhaloaromatic compound is added later), the amount of polyhaloaromatic compound relative to boron trihalide and preferences therefor are the same as those described for the relative amounts of Grignard reagent to boron trihalide.

The order in which the components are brought together does not affect the outcome of the process. For example, all of the components can be brought together simultaneously; the boron trihalide and the $^F$aryl Grignard reagent can be mixed and then the mixture can be brought into contact with the copper compound; the copper compound can be mixed with the boron trihalide and then this mixture can be brought into contact with the $^F$aryl Grignard reagent; or the copper compound can be mixed with the $^F$aryl Grignard reagent and then this mixture can be brought into contact with the boron trihalide. A preferred way of conducting the processes of this invention is to mix the copper compound with the $^F$aryl Grignard reagent in the anhydrous liquid organic medium and then bring this mixture into contact with the boron trihalide.

Another way of conducting the processes of this invention is to mix the copper compound and magnesium metal (in the anhydrous liquid organic medium), this mixture can be brought into contact with the boron trihalide, and the resultant mixture can be brought into contact with the polyhaloaromatic compound; alternatively the boron trihalide and the polyhaloaromatic compound can be in admixture when brought into contact with the mixture formed from the copper compound and magnesium metal in the anhydrous liquid organic medium. Still another way of conducting the processes of this invention is to mix the boron trihalide and the copper compound, this mixture can be brought into contact with magnesium metal, and the resultant mixture can be brought into contact with the polyhaloaromatic compound. In these processes in which the polyhaloaromatic compound is brought into contact with the mixture later, the concentration of the thermally sensitive $^F$aryl Grignard reagent is kept low, allowing the reaction to proceed at lower temperatures and without need for high-pressure equipment.

The temperatures for conducting the processes of this invention may range from about −20° C. to about 60° C.; preferable is a range from about 15° C. to about 35° C. Generally and preferably, the process is conducted at ambient temperatures (about 18° C. to about 25° C.). Ambient temperatures are preferred because the yield of the halomagnesium tetrakis($^F$aryl)borate is usually much higher than when the mixture is heated. During the course of the reaction, some heat may be produced, raising the temperature of the reaction mixture. The mixture may be heated, although as noted, decreased yields are observed for processes at elevated temperatures.

A contact time for the components of the process is typically in the range of about ten minutes to about five hours. Preferably, the contact time is about fifteen minutes to about three hours. More preferred is a contact time in the range of about 30 minutes to about two hours.

The product mixture is normally comprised of a liquid organic medium, magnesium salts, copper compounds, and at least one halomagnesium tetrakis($^F$aryl)borate. The liquid organic medium is as described above for the processes of this invention, including the preferences therefor. Magnesium salts include at least bromide, fluoride, and mixed salts.

Halomagnesium tetrakis($^F$aryl)borates produced in the processes of this invention have a tetrakis($^F$aryl)borate anion comprised of a boron atom and four $^F$aryl groups, which $^F$aryl groups are as described above. In the halomagnesium moiety of the halomagnesium tetrakis($^F$aryl)borate, the halogen atom may be a chlorine atom, bromine atom, or iodine atom, and is determined by the halogen atoms present in the reaction mixture, which include at least the halogen atoms of the $^F$aryl Grignard reagent.

When a preferred Grignard reagent is employed in the process, the corresponding halomagnesium tetrakis($^F$aryl) borates are chloromagnesium tetrakis(pentafluorophenyl) borate, bromomagnesium tetrakis(pentafluorophenyl)borate, chloromagnesium tetrakis(nonafluoro-1-biphenyl-4-yl)borate, bromomagnesium tetrakis(nonafluoro-1-biphenyl-4-yl) borate, chloromagnesium tetrakis(nonafluoro-1-biphenyl-3-yl)borate, bromomagnesium tetrakis(nonafluoro-1-biphenyl-3-yl)borate, bromomagnesium tetrakis(1-heptafluoronaphthyl)borate, chloromagnesium tetrakis(1-heptafluoronaphthyl)borate, bromomagnesium tetrakis(2-heptafluoronaphthyl)borate, chloromagnesium tetrakis(2-heptafluoronaphthyl)borate, bromomagnesium tetrakis(7-nonafluoroanthryl)borate, chloromagnesium tetrakis(7-nonafluoroanthryl)borate, bromomagnesium tetrakis(9-nonafluorophenanthryl)borate, or chloromagnesium tetrakis (9-nonafluorophenanthryl)borate. For more preferred processes, the product mixture contains the corresponding halomagnesium tetrakis($^F$aryl)borates, which are bromomagnesium tetrakis(1-heptafluoronaphthyl)borate, chloro magnesium tetrakis(1-heptafluoronaphthyl)borate, bromomagnesium tetrakis(2-heptafluoronaphthyl)borate, chloromagnesium tetrakis(2-heptafluoronaphthyl)borate, chloromagnesium tetrakis(pentafluorophenyl)borate, and bromomagnesium tetrakis(pentafluorophenyl)-borate, especially bromomagnesium tetrakis(1-heptafluoronaphthyl)borate, bromomagnesium tetrakis(2-heptafluoronaphthyl)borate, chloromagnesium tetrakis(pentafluorophenyl)borate, and bromomagnesium tetrakis(pentafluorophenyl)-borate.

Other possible constituents of the product mixture may include one or more hydrocarbons, polyfluorohydrocarbons, halopolyfluorocarbons and/or unreacted $^F$aryl Grignard reagent. When the $^F$aryl Grignard reagent is formed from a hydrocarbyl Grignard reagent and a polyhaloaromatic compound, one or more hydrocarbyl halides and/or di($^F$aryl) haloboranes may be present in the product mixture. For example, when the $^F$aryl Grignard reagent is pentafluorophenyl bromomagnesium, and it was prepared from isopropyl magnesium bromide and bromopentafluorobenzene, isopropyl bromide is a hydrocarbyl halide that may be present; pentafluorobenzene is a polyfluorohydrocarbon that can be present; and bromopentafluorobenzene is a halopolyfluorocarbon that may be present. When boron trifluoride or a solvent complex thereof and a preferred $^F$aryl Grignard reagent are employed in the process, the respective corresponding di($^F$aryl)haloborane side products are di(pentafluorophenyl)fluoroborane, di(nonafluoro-1-biphenyl-4-yl) fluoroborane, di(nonafluoro-1-biphenyl-3-yl)fluoroborane, di(1-heptafluoronaphthyl)fluoroborane, di(2-heptafluoronaphthyl)fluoroborane, di(7-nonafluoroanthryl)fluoroborane, or di(9-nonafluorophenanthryl)fluoroborane. In more preferred processes, the product mixture contains di(1-heptafluoronaphthyl)fluoroborane, di(2-heptafluoronaphthyl) fluoroborane, or di(pentafluorophenyl)fluoroborane as the di($^F$aryl)haloborane side product.

Compositions of this invention include halomagnesium tetrakis(1-heptafluoronaphthyl)borates or a halomagnesium tetrakis(2-heptafluoronaphthyl)borates, more particularly chloromagnesium tetrakis(1-heptafluoronaphthyl)borate or bromomagnesium tetrakis(1-heptafluoronaphthyl)borate, chloromagnesium tetrakis(2-heptafluoronaphthyl)borate or bromomagnesium tetrakis(2-heptafluoronaphthyl)borate. Preferred compositions include bromomagnesium tetrakis (2-heptafluoronaphthyl)borate.

Alkali metal salts of the tetrakis($^F$aryl)borate can be formed by reacting a halomagnesium tetrakis($^F$aryl)borate with, for example an alkali metal fluoride or an alkali metal carbonate or bicarbonate; see in this connection U.S. Pat. No. 6,162,950 and U.S. Pat. No. 6,831,200. From the alkali metal tetrakis($^F$aryl)borates, a variety of other salts can be made, such as a protic ammonium salt, an onium salt, or a triarylmethyl salt. When the organic cation is an onium cation, the tetrakis($^F$aryl)borate salt is useful as an initiator in crosslinking polyorganosiloxanes.

A note of caution regarding the alkali metal salts of the tetrakis($^F$aryl)borates: when dry, alkali metal tetrakis($^F$aryl) borates are both thermally sensitive and sensitive to shock. One way to mitigate these sensitivities is described in U.S. Pat. No. 6,831,200.

A large variety of metal salts of the tetrakis($^F$aryl)borate anion may be produced, either directly from the halomagnesium tetrakis($^F$aryl)borate or via magnesium di[tetrakis ($^F$aryl)borate], as described in U.S. Pat. No. 6,169,208. The cation of the metal salt may be an alkali metal cation, an alkaline earth cation other than magnesium, or a transition metal cation (see U.S. Pat. No. 6,169,208 and U.S. Pat. No. 6,831,200). These other salts of the tetrakis($^F$aryl)borate can then be reacted to form a protic ammonium salt, an onium salt, or a triarylmethyl salt.

The following examples are presented for purposes of illustration, and are not intended to impose limitations on the scope of this invention.

Unless otherwise noted, all procedures in the Examples were conducted at ambient conditions (atmospheric pressure and temperatures of about 18-25° C.) in a drybox with a nitrogen atmosphere using anhydrous solvents.

Example 1—Comparative

To a solution of isopropyl magnesium bromide in diethyl ether (approximately 20 wt %, 26.1 g) were added 8.2 g of bromopentafluorobenzene with stirring. The mixture was sampled after approximately 4 hours after all the bromopentafluorobenzene had been added; a $^{19}$F NMR spectrum of this solution showed 99.4% of the bromopentafluorobenzene had been converted to pentafluorophenyl magnesium bromide. Approximately 1.1 g of boron trifluoride etherate were added dropwise to the mixture with stirring; the reaction was exothermic. The resulting mixture was allowed to stir for 2 hours at room temperature, after which a small amount of the mixture (approximately 1 mL) was removed and set aside for NMR analysis. After another 1.5 hours, this small amount of the mixture was analyzed by $^{19}$F NMR spectroscopy, and found to contain a large amount of tris(pentafluorophenyl)borane and unreacted pentafluorophenyl magnesium bromide; little tetrakis(pentafluorophenyl)borate was detected.

Example 2

Approximately 0.05 g of copper(I) bromide was added with stirring to the bulk of the mixture prepared in Example 1. After stirring for 1.5 hours, the bulk of the mixture was sampled for NMR spectroscopy. Fluorine NMR spectroscopy showed that the copper bromide-treated mixture contained only tetrakis(pentafluorophenyl)borate; no tris(pentafluorophenyl)borane was observed.

Example 3

A solution of pentafluorophenyl magnesium bromide (19.2 g) in diethyl ether (74.3 g) prepared from isopropylmagnesium bromide and bromopentafluorobenzene, and containing copper(I) bromide (0.037 g), was treated with boron trifluoride etherate (2.45 g) dropwise with stirring over approximately 5 minutes. After another 30 minutes, a fluorine NMR spectrum on a sample from this solution showed only tetrakis(pentafluorophenyl)borate; no tris(pentafluorophenyl)borane was observed.

Example 4—Comparative

An ether solution of pentafluorophenyl magnesium bromide weighing 103.5 g was prepared by adding bromopentafluorobenzene (23.2 g) to an equimolar amount of isopropyl magnesium bromide in ether. This mixture was treated with 3.3 g of boron trifluoride etherate. After 4 hours, a fluorine NMR spectrum of this solution showed unreacted pentafluorophenyl magnesium bromide and tris(pentafluorophenyl)borane, with very little tetrakis(pentafluorophenyl)borate.

The solution prepared in this Example served as the stock solution for the experiments in Examples 5-8.

Example 5

Copper(I) chloride (0.028 g) was placed in a 20 mL vial. A portion of the stock solution prepared in Example 4 (10.2 g) was added to the vial, and the vial was shaken for 5-10 minutes to mix the contents of the vial. A fluorine NMR spectrum recorded less than 45 minutes after the mixing with copper chloride showed complete conversion to tetrakis(pentafluorophenyl)borate, with no tris(pentafluorophenyl)borane remaining.

Example 6

Copper(II) bromide (0.012 g) was placed in a 20 mL vial. A portion of the stock solution prepared in Example 4 (6.6 g) was added to the vial, and the vial was shaken for 5-10 minutes to mix the contents of the vial. A fluorine NMR spectrum recorded less than 45 minutes after the mixing with copper bromide was finished showed complete conversion to tetrakis(pentafluorophenyl)borate, with no tris (pentafluorophenyl)borane present.

Example 7

Copper(I) tris(triphenylphosphine) bromide (0.037 g) was placed in a 20 mL vial. A portion of the stock solution prepared in Example 4 (6.7 g) was added to the vial, and the vial was shaken for 5-10 minutes to mix the contents of the vial. A fluorine NMR spectrum recorded less than 45 minutes after the mixing with copper(I) tris(triphenylphosphine) bromide was finished showed complete conversion to tetrakis(pentafluorophenyl)borate, with no tris(pentafluorophenyl)borane remaining.

Example 8

Copper(II) chloride (0.016 g) was placed in a 20 mL vial. A portion of the stock solution prepared in Example 4 (7.7 g) was added to the vial, and the vial was shaken for 5-10 minutes to mix the contents of the vial. A fluorine NMR spectrum recorded less than 45 minutes after the mixing with copper chloride was finished showed complete conversion to tetrakis(pentafluorophenyl)borate, with no tris(pentafluorophenyl)borane evident.

Example 9

Magnesium metal (5.29 g) was placed in approximately 200 g of diethyl ether. While stirring, 42.1 g of bromopentafluorobenzene were added dropwise to the $Mg^0$ while maintaining an ether reflux. The mixture was stirred for another 1.5 hours after the bromopentafluorobenzene addition while continuing to maintain an ether reflux, to complete the formation of pentafluorophenyl bromomagnesium. No peaks for bromopentafluorobenzene were observed in a fluorine NMR spectrum of a sample of this mixture.

The mixture was then treated, while stirring, with 0.91 g of copper(I) bromide, and stirred for 45 minutes after the copper bromide addition. Then the mixture was chilled to −7° C., and 7.93 g of boron trifluoride etherate were added with stirring while maintaining the temperature of the solution below 3° C. The reaction mixture was allowed to warm up to ambient temperature and sampled after 3.5 hours. A fluorine NMR spectrum of the sample showed the presence of di(pentafluorophenyl)fluoroborane and tetrakis(pentafluorophenyl)borate species; no tris(pentafluorophenyl)borane was evident.

Example 10—Comparative

A solution of 2-heptafluoronaphthyl bromomagnesium in diethyl ether was prepared by adding 29.9 g of 2-bromoheptafluoronaphthalene in solid portions over 30 minutes to 71.7 g of an approximately 18.8 wt % isopropylmagnesium bromide solution in diethyl ether. The reaction was exothermic. Fluorine NMR spectroscopy indicated about 96% reaction completion. An additional 2.2 g of isopropylmagnesium bromide solution were added to take the reaction further to completion. The mixture was treated with 3.16 g of boron trifluoride etherate dropwise over 10 minutes; the reaction was exothermic. The mixture was allowed to cool to ambient temperature and was stirred overnight, then sampled for NMR analysis. A fluorine NMR spectrum showed the presence of 2-heptafluoronaphthyl bromomagnesium. No tetrakis(2-heptafluoronaphthyl)borate was observed.

Example 11

The solution in Example 10 was treated while stirring with 0.076 g of copper(I) bromide. After an additional 30 minutes of stirring, a sample was taken for NMR analysis. A fluorine NMR spectrum did not show peaks for 2-heptafluoronaphthyl bromomagnesium, but did show tetrakis(2-heptafluoronaphthyl)borate.

Example 12

Magnesium metal (1.65 g) and diethyl ether (84.5 g) were added to a flask and stirred for 3.5 hours, and then copper(I) bromide (0.055 g) was added. The mixture was stirred for an additional 15 minutes. Next, boron trifluoride etherate (1.93 g) was added dropwise over about 2 minutes, and the resulting mixture was stirred for an additional 25 minutes.

Then, while stirring, 13.4 g of bromopentafluorobenzene was added dropwise over 40 minutes to sustain an exotherm at the temperature of refluxing solvent (34-36° C.). Once the addition was complete, the mixture was allowed to cool to room temperature (~22° C.) over 1 hour. An aliquot was filtered for analysis. A fluorine NMR spectrum showed a ratio of pentafluorophenyl groups of tetrakis(pentafluorophenyl)borate to unreacted pentafluorophenylmagnesium bromide of approx. 52:1. No tris(pentafluorophenyl)borane was observed, although some bis(pentafluorophenyl)boron ethoxide (9-10 mol % relative to tetrakis(pentafluorophenyl) borate) was present. Over time, this ethoxide reacted at room temperature with the remaining pentafluorophenylmagnesium bromide to form additional tetrakis(pentafluorophenyl) borate. In the end, no pentafluorophenylmagnesium bromide was seen in the reaction mixture.

Example 13—Comparative

Magnesium metal (2.7 g) was slurried in diethyl ether (70 g), and boron trifluoride etherate (3.26 g) was added. The stirring mixture was treated with bromopentafluorobenzene (25.0 g) over 30 minutes while maintaining the temperature around 25° C. The reaction mixture was stirred for an additional 2 hours, and the supernatant liquid was sampled for analysis. Fluorine NMR analysis showed little, if any, tetrakis(pentafluorophenyl)borate species, and showed tris (pentafluorophenyl)borane, bis(pentafluorophenyl)boron ethoxide, and unreacted pentafluorophenylmagnesium bromide.

The mixture was transferred to a Fischer Porter bottle, and heated at 60° C. overnight. After cooling to room temperature, the mixture was filtered, and a sample of the solution was taken for analysis. Fluorine NMR analysis showed a ratio of pentafluorophenyl groups of tetrakis(pentafluorophenyl)borate to tris(pentafluorophenyl)borane to unreacted pentafluorophenylmagnesium bromide of approx. 4.9:1.7:1, meaning a large amount of pentafluorophenylmagnesium bromide and tris(pentafluorophenyl)borane were still present, even after prolonged heating.

Regarding Examples 2-3, 5-9, 11, and 12, the tetrakis ($^F$aryl)borate product was obtained, but no tris($^F$aryl)borane was observed. In Examples 2-3, 5-8, and 11, the copper compound did not catalyze a coupling reaction of the perfluoroaryl bromomagnesium species with byproduct isopropyl bromide still present in solution. The conversion to bromomagnesium tetrakis(perfluoroaryl)borate was complete in about 2 hours or less in Examples 2-3, 5-8, and 11.

More generally, these Examples show the effectiveness of using copper compounds as catalysts for the reaction of $^F$aryl halomagnesium, particularly perfluoroaryl bromomagnesium, with boron trifluoride at ambient pressure and temperature (18-25° C.), or lower temperatures, in diethyl ether solvent to form halomagnesium tetrakis($^F$aryl)borates, particularly bromomagnesium tetrakis(perfluoroaryl)borates. The Examples above show that copper-catalyzed reactions are complete in about 2 hours or less. In comparison, uncatalyzed reactions do not produce appreciable amounts of bromomagnesium tetrakis($^F$aryl)borate at ambient temperatures. Typically, the non-catalyzed reaction requires several hours at elevated temperatures (typically 35° C. or above). See in this connection U.S. Pat. No. 6,129,863. Thus, the copper-catalyzed processes of this invention can produce tetrakis($^F$aryl)borates with high yields at reduced temperatures and reaction times as compared to non-catalyzed processes, thereby realizing significant cost savings.

Further embodiments of this invention include:

A) A process comprising bringing together, in an anhydrous liquid organic medium,
   at least one boron trihalide;
   at least one $^F$aryl Grignard reagent; and
   at least one copper compound,
   to form a halomagnesium tetrakis($^F$aryl)borate.

B) A process comprising bringing together, in an anhydrous liquid organic medium,
   at least one boron trihalide;
   at least one copper compound;
   magnesium metal; and
   at least one polyhaloaromatic compound,
   to form a halomagnesium tetrakis($^F$aryl)borate.

C) A process as in B) wherein either
   i) at least one boron trihalide, magnesium metal, and at least one copper compound are brought together to form a mixture, and
   ii) at least a portion of the mixture formed in i) and at least one polyhaloaromatic compound are brought together;
   or
   a) at least one copper compound and magnesium metal are brought together to form a mixture, and
   b) at least a portion of the mixture formed in a) and a mixture of at least one boron trihalide and at least one polyhaloaromatic compound are brought together.

D) A process as in A) wherein when an $^F$aryl Grignard reagent is used,
   the copper compound is in an amount that provides about 0.001 mmol or more of copper per mole of $^F$aryl Grignard reagent;
   the $^F$aryl Grignard reagent is pentafluorophenyl chloromagnesium, pentafluorophenyl bromomagnesium, heptafluoronaphthyl chloromagnesium, or heptafluoronaphthyl bromomagnesium; and/or
   the $^F$aryl Grignard reagent and the boron trihalide are in amounts that provide a molar ratio of about 3.9:1 to about 4.5:1.

E) A process as in any of A)-D) wherein the copper compound is a copper(I) halide and/or a copper(II) halide.

F) A process as in any of A)-D) wherein the copper compound is selected from copper(I) chloride, copper(I) bromide, bromotris(triphenylphosphine)copper(I), copper(II) chloride, copper(II) bromide, or mixtures of any two or more of the foregoing.

G) A process as in A) or D) wherein the copper compound is in an amount that provides about 0.001 mmol to about 40 mmol of copper per mole of $^F$aryl Grignard reagent.

H) A process as in any of B) or C) wherein
   the polyhaloaromatic compound is chloropentafluorobenzene, bromopentafluorobenzene, chloroheptafluoronaphthylene, or bromoheptafluoronaphthylene;
   the copper compound is in an amount that provides about 0.001 mmol or more of copper per mole of polyhaloaromatic compound; and/or
   the polyhaloaromatic compound and the boron trihalide are in amounts that provide a molar ratio of about 3.9:1 to about 4.5:1.

I) A process as in H) wherein the copper compound is in an amount that provides about 0.001 mmol to about 40 mmol of copper per mole of polyhaloaromatic compound.

J) A process as in any of A)-I) wherein the liquid organic medium is an ether-containing medium, and/or wherein the boron trihalide is boron trifluoride or a boron trifluoride-solvent complex.

K) A process as in J) wherein the ether-containing medium contains diethyl ether.

L) A process as in any of A), B), C), D), or J) wherein the boron trihalide is boron trifluoride diethyl etherate complex.

M) A process as in any of A)-L) wherein the process is conducted at a temperature in the range of about −20° C. to about 60° C.

N) A product mixture comprising a liquid organic medium, magnesium salts, copper compounds, and at least one halomagnesium tetrakis($^F$aryl)borate.

O) A product mixture as in N) wherein the halomagnesium tetrakis($^F$aryl)borate is chloromagnesium tetrakis(pentafluorophenyl)borate, bromomagnesium tetrakis(pentafluorophenyl)borate, chloromagnesium tetrakis(heptafluoronaphthyl)-borate, or bromomagnesium tetrakis(heptafluoronaphthyl)borate.

P) A product mixture as in N) or O) which further comprises an $^F$aryl Grignard reagent.

Q) A product mixture as in P) wherein the $^F$aryl Grignard reagent is pentafluorophenyl chloromagnesium, pentafluorophenyl bromomagnesium, heptafluoronaphthyl chloromagnesium, or heptafluoronaphthyl bromomagnesium.

R) A product mixture as in any of N)-Q) wherein the liquid organic medium is an ether-containing medium.

S) A product mixture as in R) wherein the ether-containing medium contains diethyl ether.

T) A composition comprising a halomagnesium tetrakis(1-heptafluoronaphthyl)borate or a halomagnesium tetrakis(2-heptafluoronaphthyl)borate.

U) A composition as in T) wherein said halomagnesium tetrakis(1-heptafluoronaphthyl)borate is chloromagnesium tetrakis(1-heptafluoronaphthyl)-borate or bromomagnesium tetrakis(1-heptafluoronaphthyl)borate, and/or wherein said halomagnesium tetrakis(2-heptafluoronaphthyl)borate is chloromagnesium tetrakis(2-heptafluoronaphthyl)borate or bromomagnesium tetrakis(2-heptafluoronaphthyl)borate.

V) A composition as in T) wherein said halomagnesium tetrakis(2-heptafluoronaphthyl)borate is bromomagnesium tetrakis(2-heptafluoronaphthyl)borate.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention may comprise, consist, or consist essentially of the materials and/or procedures recited herein.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

The invention claimed is:

1. A process comprising bringing together, in an anhydrous liquid organic medium, either
    A) at least one boron trihalide;
        at least one $^F$aryl Grignard reagent; and
        at least one copper compound,
    or
    B) at least one boron trihalide;
        at least one copper compound;
        magnesium metal; and
        at least one polyhaloaromatic compound,
    to form a halomagnesium tetrakis($^F$aryl)borate.

2. A process as in claim 1 wherein in B) either
    i) at least one boron trihalide, magnesium metal, and at least one copper compound are brought together to form a mixture, and
    ii) at least a portion of the mixture formed in i) and at least one polyhaloaromatic compound are brought together;
    or
    a) at least one copper compound and magnesium metal are brought together to form a mixture, and
    b) at least a portion of the mixture formed in a) and a mixture of at least one boron trihalide and at least one polyhaloaromatic compound are brought together.

3. A process as in claim 1 wherein in A),
    the copper compound is in an amount that provides about 0.001 mmol or more of copper per mole of $^F$aryl Grignard reagent;
    the $^F$aryl Grignard reagent is pentafluorophenyl chloromagnesium, pentafluorophenyl bromomagnesium, heptafluoronaphthyl chloromagnesium, or heptafluoronaphthyl bromomagnesium; and/or the $^F$aryl Grignard reagent and the boron trihalide are in amounts that provide a molar ratio of about 3.9:1 to about 4.5:1.

4. A process as in claim 1 wherein the copper compound is a copper(I) halide and/or a copper(II) halide.

5. A process as in claim 1 wherein the copper compound is selected from copper(I) chloride, copper(I) bromide, bromotris(triphenylphosphine)copper(I), copper(II) chloride, copper(II) bromide, or mixtures of any two or more of the foregoing.

6. A process as in claim 3 wherein the copper compound is in an amount that provides about 0.001 mmol to about 40 mmol of copper per mole of $^F$aryl Grignard reagent.

7. A process as in claim 1 wherein in B)
the polyhaloaromatic compound is chloropentafluorobenzene, bromopentafluorobenzene, chloroheptafluoronaphthylene, or bromoheptafluoronaphthylene;

the copper compound is in an amount that provides about 0.001 mmol or more of copper per mole of polyhaloaromatic compound; and/or the polyhaloaromatic compound and the boron trihalide are in amounts that provide a molar ratio of about 3.9:1 to about 4.5:1.

8. A process as in claim 7 wherein the copper compound is in an amount that provides about 0.001 mmol to about 40 mmol of copper per mole of polyhaloaromatic compound.

9. A process as in claim 1 wherein the liquid organic medium is an ether-containing medium, and/or wherein the boron trihalide is boron trifluoride or a boron trifluoride-solvent complex.

10. A process as in claim 1 wherein the boron trihalide is boron trifluoride diethyl etherate complex.

11. A process as in claim 1 wherein the process is conducted at a temperature in the range of about −20° C. to about 60° C.

\* \* \* \* \*